US008652047B2

(12) United States Patent
Kim et al.

(10) Patent No.: US 8,652,047 B2
(45) Date of Patent: Feb. 18, 2014

(54) APPARATUS AND METHOD FOR AUTOMATICALLY MEASURING THE VOLUME OF URINE IN A BLADDER USING ULTRASOUND SIGNALS

(75) Inventors: Jung-Hoe Kim, Seoul (KR); Seung-Tai Kim, Seoul (KR)

(73) Assignee: Mcube Technology Co., Ltd. (KR)

( * ) Notice: Subject to any disclaimer, the term of this patent is extended or adjusted under 35 U.S.C. 154(b) by 194 days.

(21) Appl. No.: 12/878,422

(22) Filed: Sep. 9, 2010

(65) Prior Publication Data
US 2010/0331696 A1 Dec. 30, 2010

Related U.S. Application Data (63) Continuation-in-part of application No. 11/651,186, filed on Jan. 9, 2007, now abandoned.

(30) Foreign Application Priority Data

Jan. 9, 2006 (KR) ........................ 10-2006-0002257

(51) Int. Cl.
*A61B 8/00* (2006.01)
(52) U.S. Cl.
USPC ........... 600/438; 600/407; 600/437; 600/442; 600/449
(58) Field of Classification Search
USPC .......................... 600/407, 437, 438, 442, 449
See application file for complete search history.

(56) References Cited

U.S. PATENT DOCUMENTS

| 4,926,871 A | 5/1990 | Ganguly et al. |
| 6,110,111 A | 8/2000 | Barnard |
| 6,676,605 B2 | 1/2004 | Barnard et al. |
| 2009/0030326 A1 | 1/2009 | Kim et al. |

FOREIGN PATENT DOCUMENTS

| KR | 20-0137995 | 3/1999 |
| WO | 00/71030 | 11/2000 |
| WO | 2007/123352 | 11/2007 |

OTHER PUBLICATIONS

"Ultrasonic Assessment of Residual Urine Volume" by J.C. Rageth et al. Urological Research. 10:57-60, 1982.*
"The Accuracy of Ultrasound in the Measurement of Changes in Bladder Volume" by G.J. Poston et al. British Journal of Urology. 55:361-363, 1983.*
J.H. Holmes, "Ultrasonic studies of the bladder," Elsevier, vol. 97, 1967, pp. 654-663.

(Continued)

*Primary Examiner* — Tse Chen
*Assistant Examiner* — Jason Ip
(74) *Attorney, Agent, or Firm* — Cantor Colburn LLP (57) ABSTRACT

The method of accurately measuring the volume of urine in a bladder includes generating a plurality of ultrasound scan planes using the received ultrasound signals; detecting distances between the front and back walls of the bladder for each scan line in the ultrasound scan planes; determining an area of the bladder using the detected distances of the scan lines for each ultrasound scan plane; generating a virtual radius of the bladder using the determined area of the bladder for each ultrasound scan plane; determining a calibration coefficient for each ultrasound scan plane using the detected distances of the scan lines; calibrating the virtual radius of the bladder for each ultrasound scan plane using the calibration coefficient; determining the volume of urine in the bladder by calculating the volume of a sphere of which the radius is the average of the calibrated virtual radii for the ultrasound scan planes.

4 Claims, 10 Drawing Sheets (56) References Cited

OTHER PUBLICATIONS

C.J.M. Beacock et al., "Ultrasound Assessment of Residual Urine," vol. 57, 1985, pp. 410-413.

C.A. Mittlestaedt, "General Ultrasound," Churchill Livingstone Inc., 1992, p. 1046.

* cited by examiner

FIG. 9D

APPARATUS AND METHOD FOR AUTOMATICALLY MEASURING THE VOLUME OF URINE IN A BLADDER USING ULTRASOUND SIGNALS This is a continuation-in-part of application Ser. No. 11/651,186 filed Jan. 9, 2007 in the names of KIM Jong Hoe and KIM Seong Tae (now abandoned).

BACKGROUND OF THE INVENTION

1. Field of the Invention

The present invention relates generally to an apparatus and method for measuring the volume of urine in a bladder using ultrasound signals, and more particularly, to an apparatus and a method which can accurately measure the volume of urine in the bladder using ultrasound signals regardless of the detection location on which a transducer is placed.

2. Description of the Related Art

Generally, an ultrasonic system is a system that emits ultrasonic signals to an object to be examined using the piezoelectric effect of a transducer, receives the ultrasonic signals reflected from the discontinuous planes of the object, converts the received ultrasonic signals into electrical signals, and outputs the electrical signals to a predetermined display device, thus enabling examination of the internal states of the object. Such an ultrasonic system is widely used for medical diagnosis equipment, non-destructive testing equipment or underwater detection equipment.

When diagnosing bladder abnormalities or urinary difficulty, measuring the volume of urine in the bladder is an essential procedure. Furthermore, prior to urination using a catheter, the volume of urine in the bladder should be measured to account for urine that may be retained after the operation. In addition, in urination training, the amount of urine in a bladder should be measured as a guideline.

Various types of ultrasonic scanning equipment may be used to measure the volume of urine in a bladder. In this case, two methods are used. A first method calculates the amount of urine from ultrasonic images for a perpendicular plane and a horizontal plane, which are obtained using typical ultrasonic scanning equipment. However, although many algorithms has been proposed and used for the first method, the first method is problematic in that it not only has a considerable error rate but also exhibits different results for different operators. A second method uses dedicated ultrasonic equipment for measuring the volume of urine in the bladder. U.S. Pat. No. 4,926,871 discloses dedicated ultrasonic equipment. However, the dedicated ultrasonic equipment based on the second method has a disadvantage in that it also calculates the amount of urine chiefly using two ultrasonic images of a bladder, and in that a operator must find an ultrasound scan plane having the area of the bladder with the greatest size and select it in order to calculate of the amount of urine.

Figure 6:
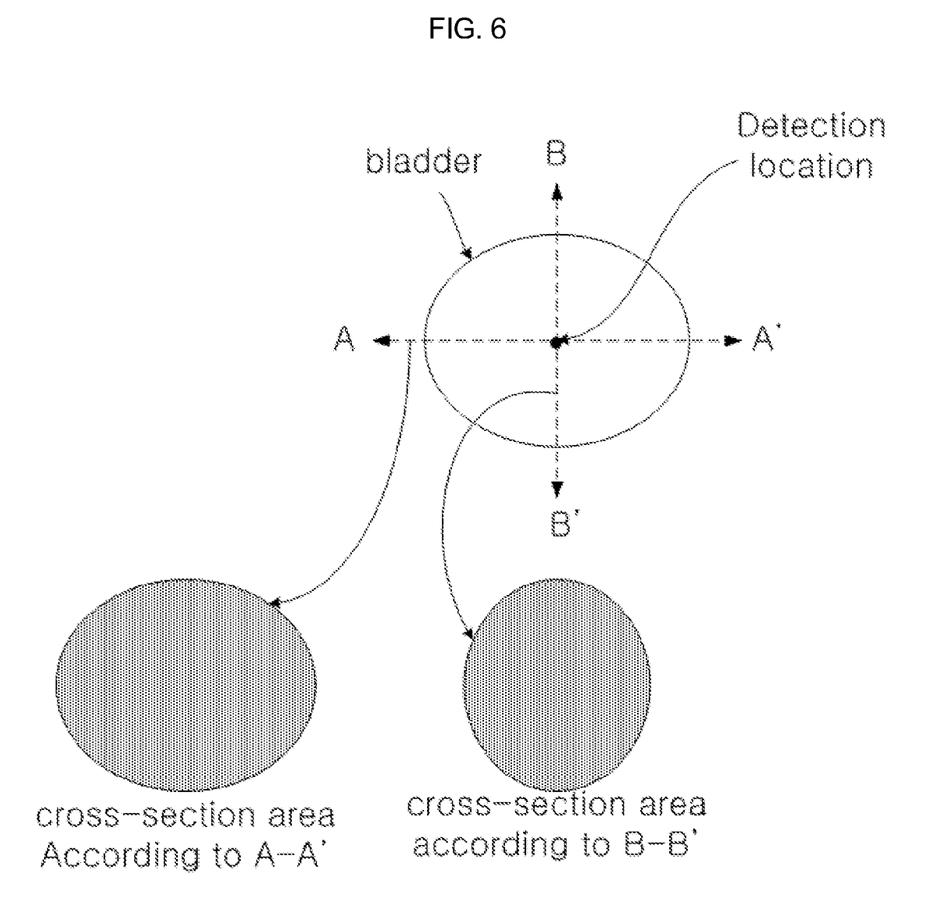
FIG. 6 is a diagram illustrating the area of bladder acquired from each of the ultrasound scan planes when the transducer of the apparatus is placed over the center of the bladder.
Figure 7:
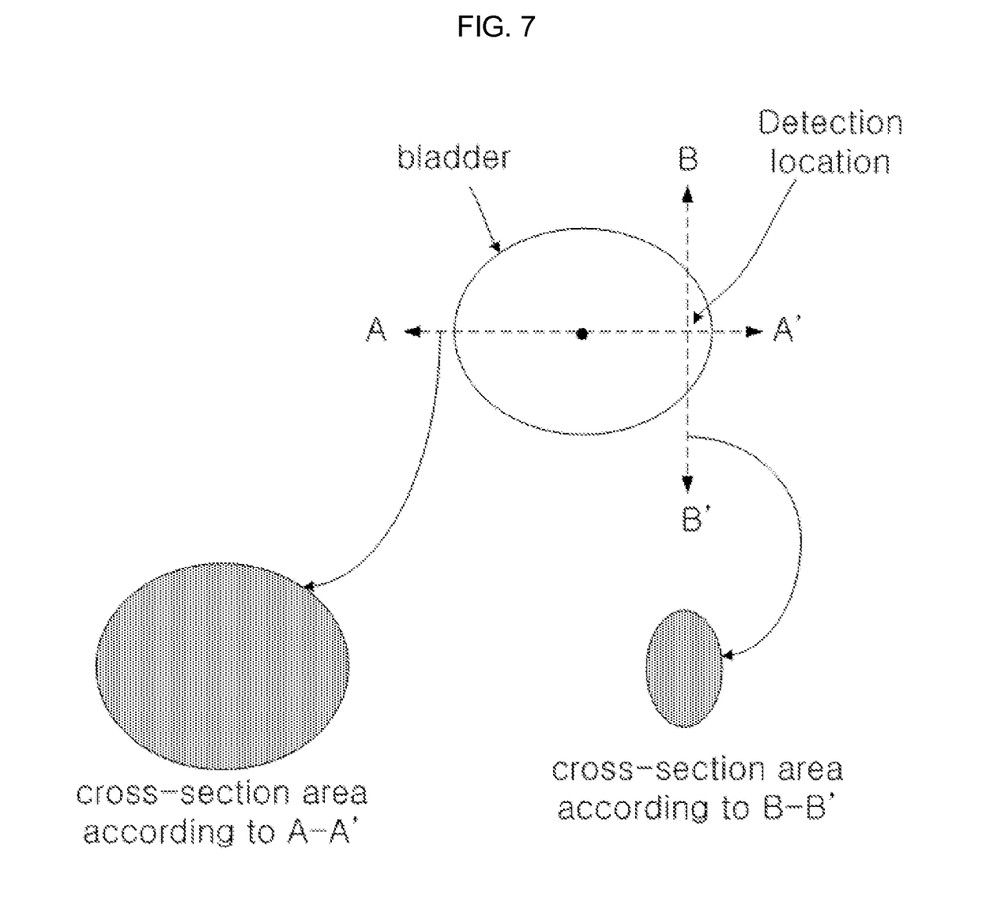
FIG. 7 is a diagram illustrating the area of bladder acquired from each of the ultrasound scan planes when the transducer of the apparatus is placed on the upper position which is moved from the center of the bladder.

FIG. 6 is a diagram showing the areas of a bladder in the ultrasound scan planes when the transducer is placed on the center of the bladder. FIG. 7 is a diagram showing the areas of a bladder in the ultrasound scan planes when the transducer is placed on the position which is moved from the center of the bladder. Referring to FIGS. 6 and 7, the cross-section areas of the bladder according to B-B' are different each other. The volume of bladder calculated using the areas of bladder can be varied according to the position where the transducer is placed.

Accordingly, the present applicant proposes a method of accurately calculating the volume of urine in a bladder while minimizing operator interference.

SUMMARY OF THE INVENTION

Accordingly, the present invention has been made keeping in mind the above problems occurring in the prior art, and an object of the present invention is to provide an apparatus for accurately measuring the volume of urine in a bladder using ultrasound signals while minimizing operator interference.

A further object of the present invention is to provide a method for accurately measuring the volume of urine in the bladder using the ultrasound signals regardless of the detection position on which the transducer is placed.

In order to accomplish the above objects, the present invention provides an apparatus for measuring a volume of urine in a bladder, including a transducer for transmitting ultrasound signals and receiving the ultrasound signals returning from a bladder and surrounding tissues; means for generating a plurality of ultrasound scan planes using the received ultrasound signals of the transducer, each of the ultrasound scan planes is separated by a selected angle and consists of a plurality of scan lines, to produce a scan cone for scanning the bladder; means for detecting distances between the front and back walls of the bladder for each scan line in the ultrasound scan planes; means for automatically determining the area of the bladder using the detected distances of the scan lines for each ultrasound scan plane; means for automatically generating a virtual radius of the bladder using the determined area of the bladder for each ultrasound scan plane; means for automatically determining a calibration coefficient for each ultrasound scan plane using the detected distances of the scan lines; means for automatically calibrating the virtual radius of a bladder for each ultrasound scan plane using the calibration coefficient; means for automatically determining the volume of urine in the bladder by calculating the volume of a sphere of which the radius is the average of the calibrated virtual radii for the ultrasound scan planes.

In addition, A method for automatically measuring the volume of urine in a bladder using ultrasound signals, comprising the steps of (a) transmitting ultrasound signals and receiving the ultrasound signals returning from a bladder and surrounding tissues; (b) generating a plurality of ultrasound scan planes using the received ultrasound signals, each of ultrasound scan planes is separated by a selected angle and consists of a plurality of scan lines, to produce a scan cone for scanning the bladder; (c) detecting distances between the front and back walls of the bladder for each scan line in the ultrasound scan planes; (d) determining an area of the bladder using the detected distances of the scan lines for each ultrasound scan plane; (e) generating a virtual radius of the bladder using the determined area of the bladder for each ultrasound scan plane; (f) determining a calibration coefficient for each ultrasound scan plane using the detected distances of the scan lines; (g) calibrating the virtual radius of the bladder for each ultrasound scan plane using the calibration coefficient; (h) determining the volume of urine in the bladder by calculating the volume of a sphere of which the radius is the average of the calibrated virtual radii for the ultrasound scan planes.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
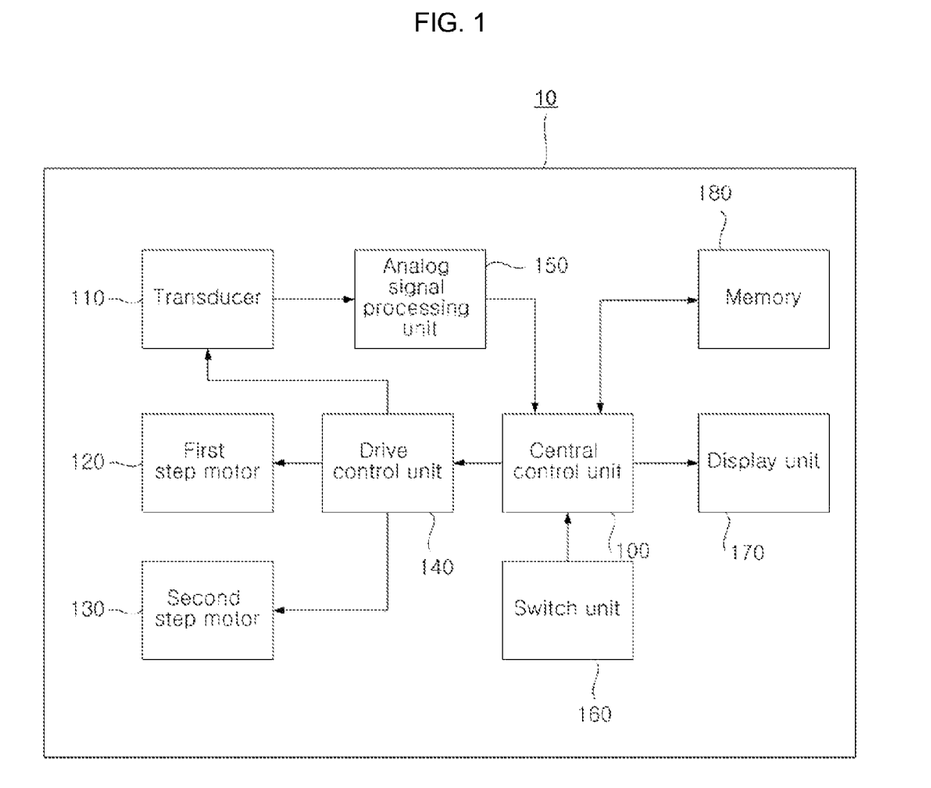
FIG. 1 is a block diagram schematically showing the internal construction of an ultrasonic scanning apparatus according to a preferred embodiment of the present invention.
Figure 2:
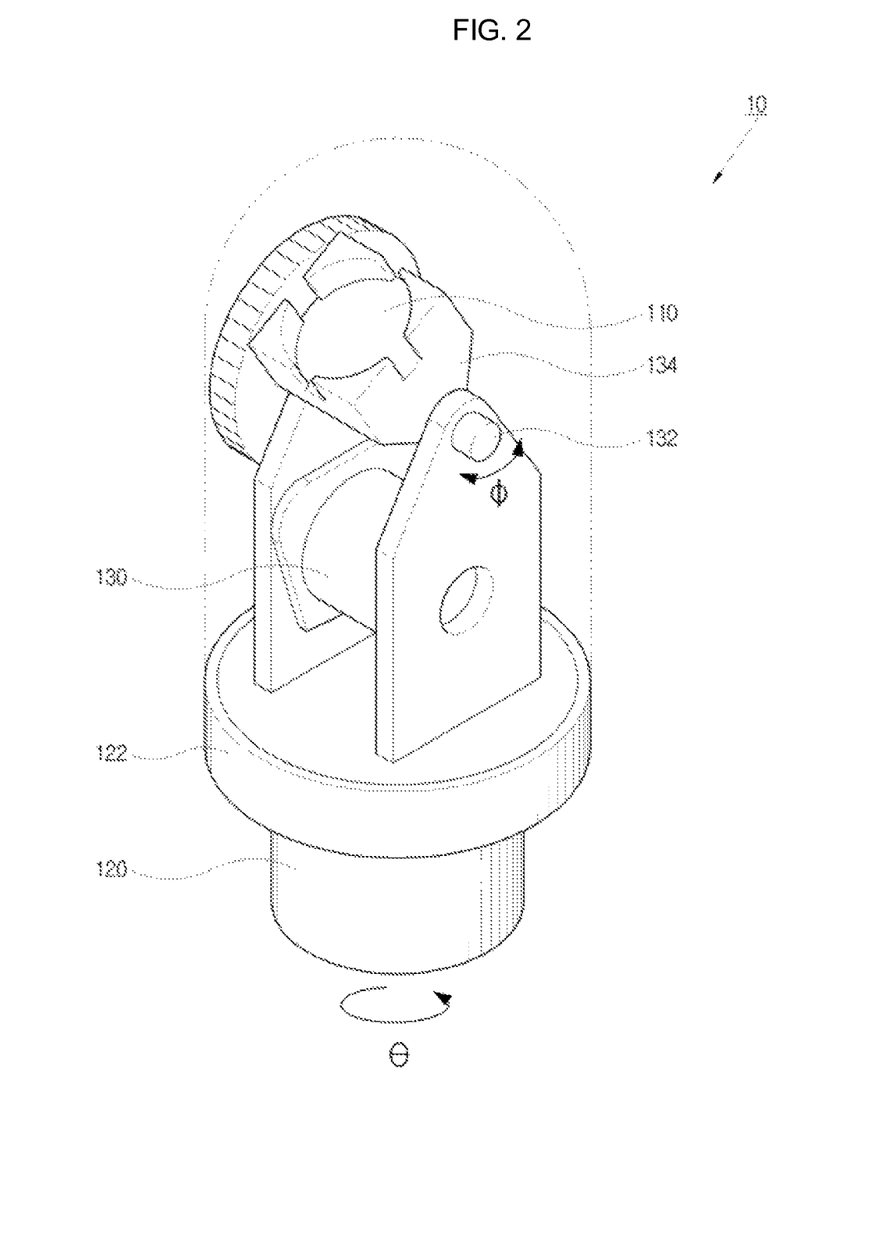
FIG. 2 is a perspective view showing the ultrasonic scanning apparatus of FIG. 1.

The construction and operation of an apparatus and method for measuring a volume of urine in a bladder according to a preferred embodiment of the present invention are described in detail with reference to the accompanying drawings. FIG. 1 is a block diagram schematically showing the internal construction of the apparatus according to a preferred embodiment of the present invention, and FIG. 2 is a perspective view showing the apparatus of FIG. 1.

Referring to FIG. 1, the apparatus 10 according to the preferred embodiment of the present invention includes a central control unit 100 for controlling the overall operation of the apparatus, a transducer 110, a first stepping motor 120, a second stepping motor 130, a drive control unit 140, an analog signal processing unit 150, a switch unit 160, memory 180, and a display unit 170. The respective components of the above-described apparatus 10 are described in detail below.

The transducer 110 is a device that emits ultrasonic signals and receives ultrasonic signals returned from the internal organs of a human body, and transmits the received analog signals to the analog signal processing unit 150. The transducer 110 according to the present invention receives ultrasonic signals returned from urine in the bladder.

The analog signal processing unit 150 converts the analog signals, which are transmitted from the transducer 110, into digital signals, and transmits the digital signals to the central control unit 100.

The central control unit 100 calculates the volume of urine in the bladder using the ultrasound signals transmitted from the analog signal processing unit 150, and outputs the calculated volume of urine in numeral form to the display unit 170. The display unit 170 displays the volume value of urine in the bladder in numeral form.

As shown in FIG. 2, a rotational support 122 is fixed to the first stepping motor 120. A second stepping motor 130 is mounted on the rotational support 122. The second stepping motor 130 is connected with a rotational axis 132, and a transducer support 134 is fixed to the rotational axis 132. A transducer 110 is installed in the transducer support 134.

The central control unit 100 transmits drive control signals to the drive control unit 140 in response to a request signal received from the switch unit 160, and the drive control unit 140 controls the motion of the first and second stepping motors 120 and 130 in response to the drive control signals, so that a plurality of ultrasound scan planes having the ultrasonic image of the bladder can be obtained through the rotation of the transducer 110.

The transducer 110 permits freedom of movement along two orthogonal axes. A pair of stepping motor, those are the first and second stepping motors 120 and 130, move the transducer 110 through a predetermined path under the drive control unit 140 control.

In the apparatus of the present invention, ultrasound signals are used to sample a plurality of ultrasound scan planes which produce a three-dimensional scan cone including the bladder. The each of the ultrasound scan planes is produced by a plurality of ultrasound scan lines which are made by the returned ultrasound signals from the bladder and surrounding tissues.

Figure 3A:
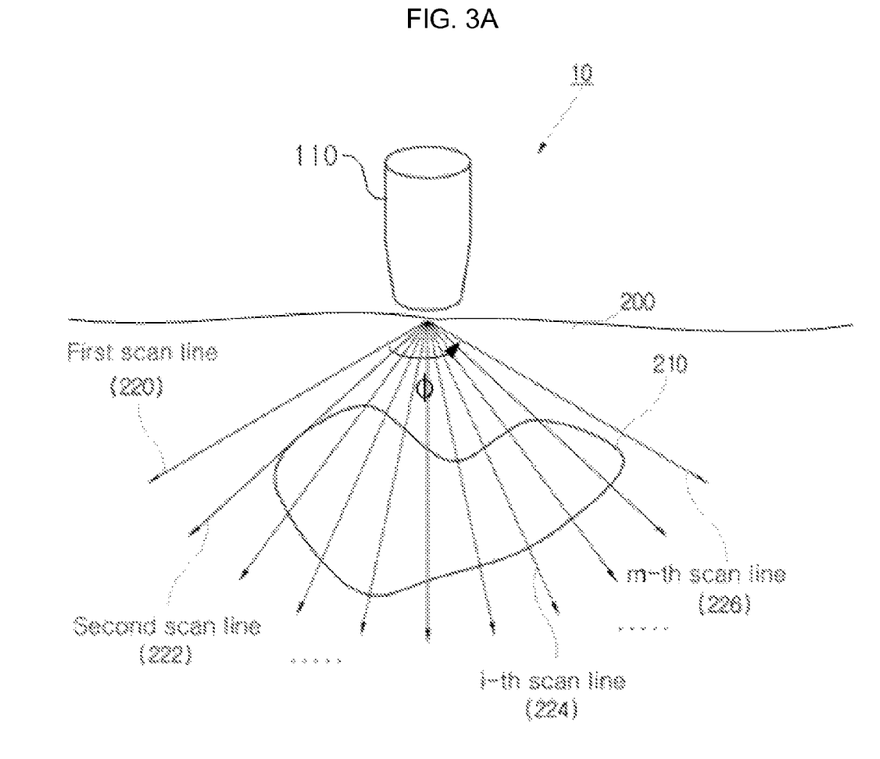
FIGS. 3A and 3B are diagrams illustrating a process of acquiring a two-dimensional ultrasound scan plane using the apparatus of FIG. 2.

The first and second stepping motors move the transducer through three-dimensional space. Referring to FIGS. 2 and 3A, the second stepping motor 130 moves the transducer 110 in the phi ($\phi$) dimension of a single scan plane. The angle between two boundary edges of the scan plane, that is a total angle phi ($\phi$), can vary, but typically will be approximately 120°. The rotational axis 132 and the transducer support 134, which are connected to the second stepping motor 130 via a gear, are rotated by the second stepping motor 130. Consequently, the transducer 110 installed in the transducer support 134 rotates in the phi ($\phi$) dimension of a single scan plane.

Figure 4:
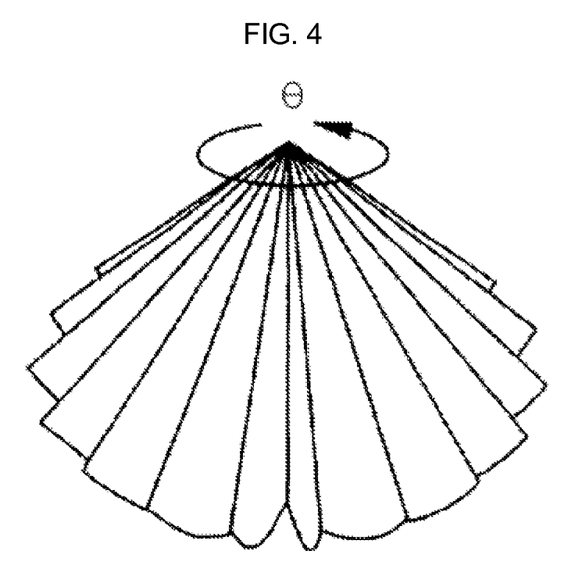
FIG. 4 is diagram illustrating a process of acquiring a ultrasound scan cone having a plurality of ultrasound scan planes using the apparatus of FIG. 2.

Referring to FIGS. 2 and 4, The first stepping motor 120 rotates the transducer assembly about a central vertical axis through a total angle theta ($\theta$) in series of small angular movements. Typically, the total angle theta will be 360°, as shown in FIG. 4. The first stepping motor rotate successively a predetermined angle in the theta direction, at each theta position an ultrasound signal scan line, along a scan plane, is generated by the transducer. The total number of ultrasound scan planes over the entire theta dimension of 360° will completely sample the imagined cone by ultrasound signals. The data, which is obtained from the ultrasound signals, is then processed to determine the location of the bladder walls in each of the ultrasound scan planes.

Figure 3B:
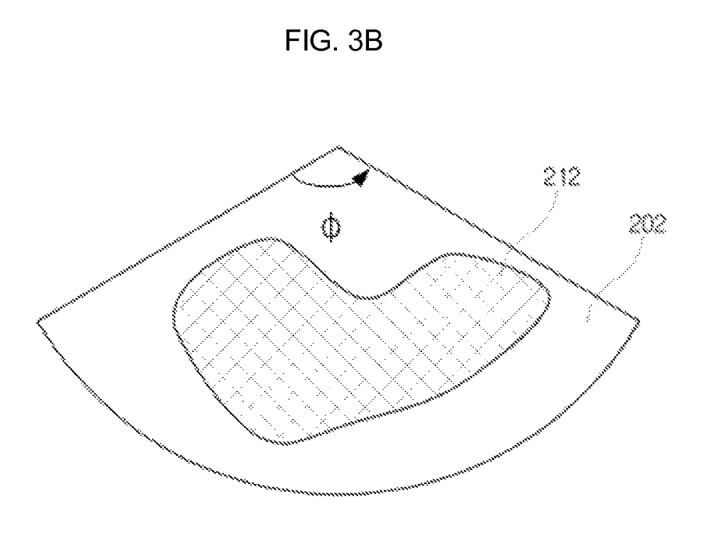

In order to measure the volume of urine in the bladder, the transducer 110 of the apparatus 10 having the above-described construction, as shown in FIG. 3A, is placed on an abdomen over the bladder 210 of a patient, and sequentially detects ultrasonic signals for a plurality of ultrasound scan planes. FIG. 3B represents an ultrasound scan plane displayed the cross-section of a bladder 212.

Each of the ultrasound scan planes includes a plurality of scan lines, that is, a first scan line 220, a second scan line, ..., an i-th scan line 224, ..., an m-th scan line 226. Each of the scan lines is made by ultrasound signals obtained by the transducer.

Figure 5:
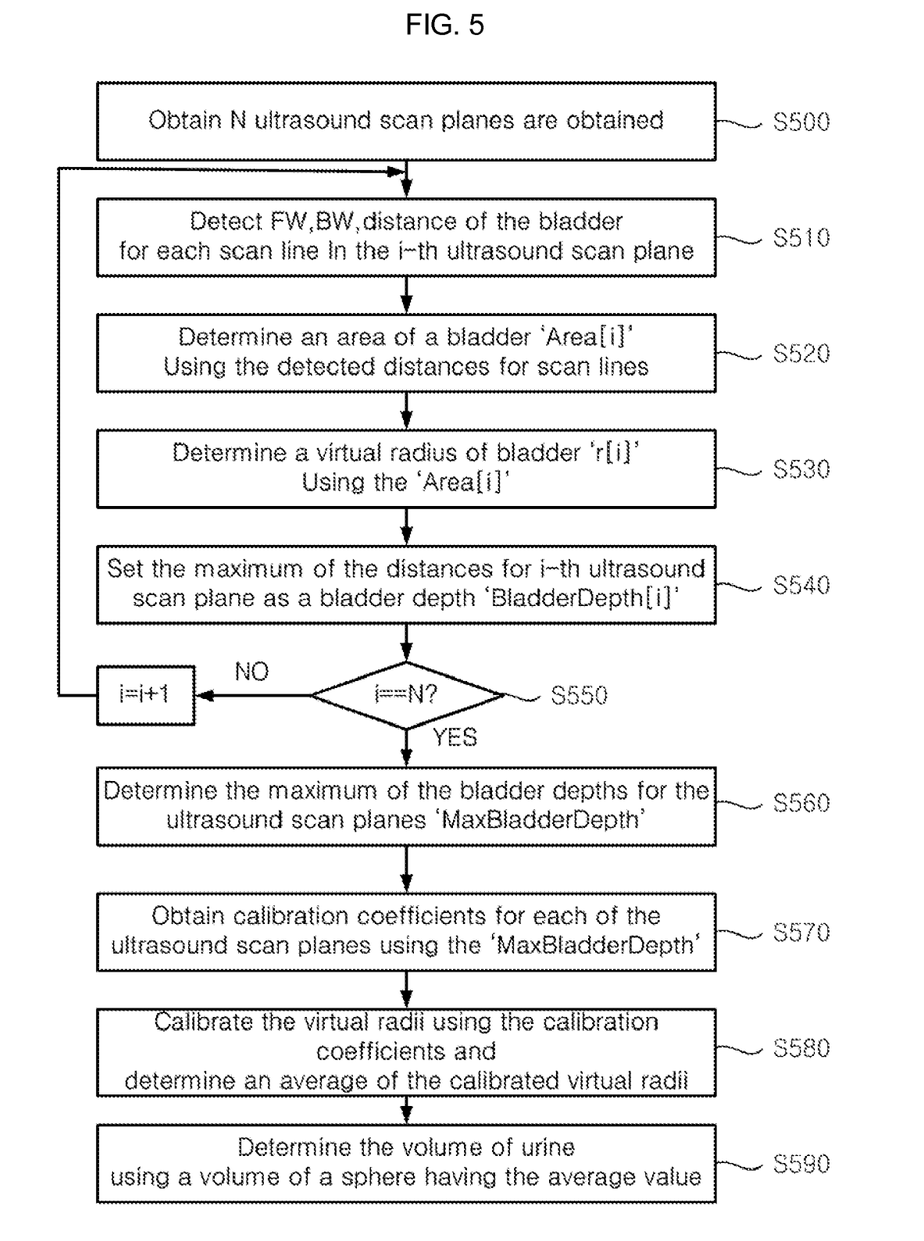
FIG. 5 is a flowchart sequentially illustrating a process of obtaining the volume of urine in a bladder using the ultrasound signals according to a preferred embodiment of the present invention.

A measuring method of the central control unit 100 according to a preferred embodiment of the present invention is described in detail below. FIG. 5 is a flowchart sequentially illustrating a process of obtaining the volume of urine in a bladder using the apparatus according to a preferred embodiment of the present invention.

The transducer 110 scans a bladder and the surrounding tissues, and transmits the ultrasound signals for ultrasound scan planes to the central control unit 100 through the analog signal processing unit 150. In a first step, shown at step s500, the central control unit 100 obtains a plurality of ultrasound scan planes. The each of ultrasound scan planes consists of ultrasound signals of a plurality of scan lines.

Figure 8:
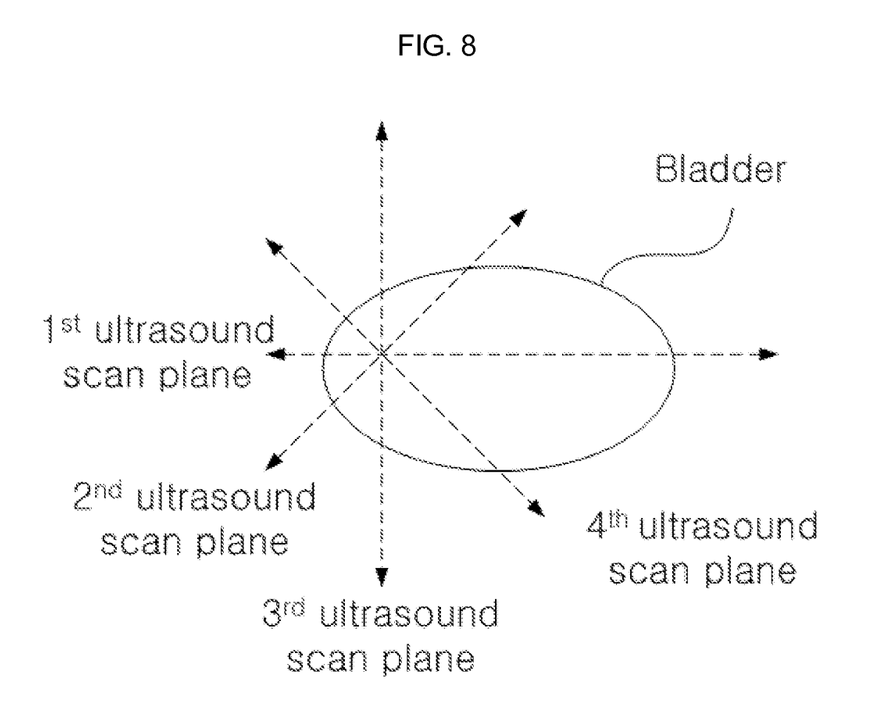
FIGS. 8, 9A, 9B, 9C and 9D are diagrams illustrating a bladder acquired from each of the ultrasound scan planes according to the present invention in order to explain the procedures of measuring the volume of urine.

FIG. 8 represents the 4 scan directions of the transducer to obtain 4 ultrasound scan planes, respectively.

Referring to FIGS. 8, 9A, 9B, 9C and 9D, the ultrasound signals of scan line contains information about the border of the bladder, specified as FW (Front wall) and BW (Back wall) of the bladder, and the distance between FW and BW of the bladder. The remaining portion of the ultrasound signals is the returning signal from the surrounding tissues.

Figure 9A:
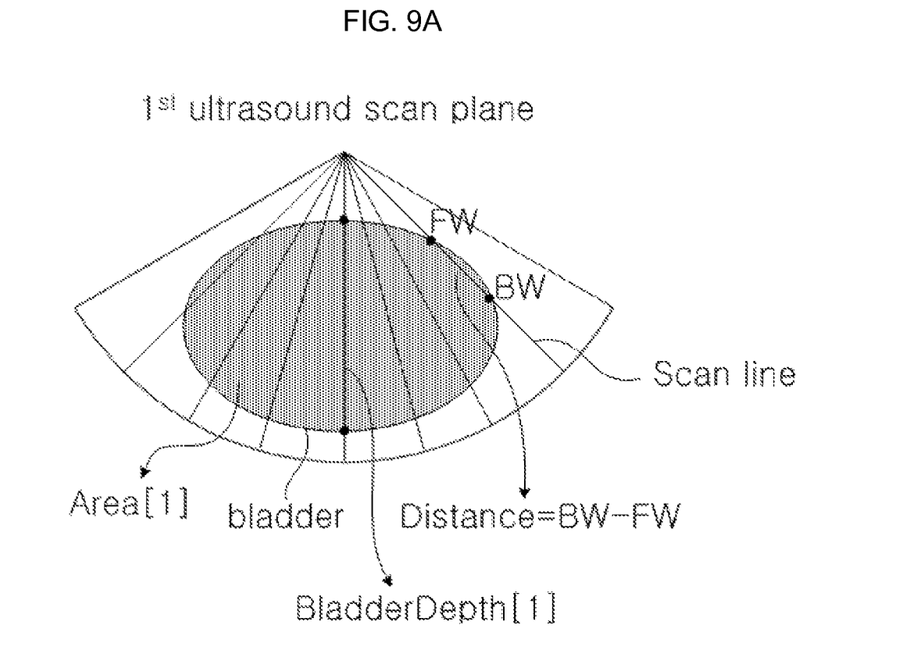
Figure 9B:
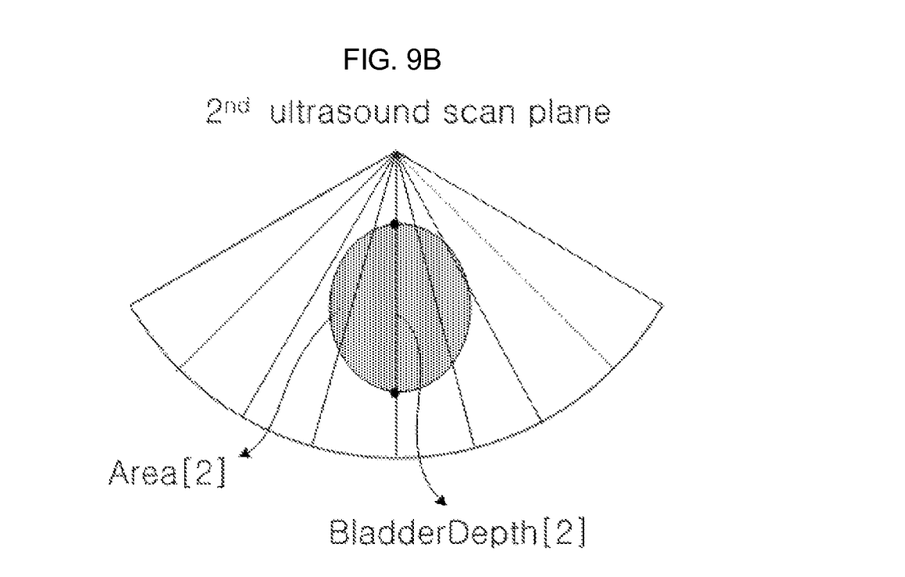
Figure 9C:
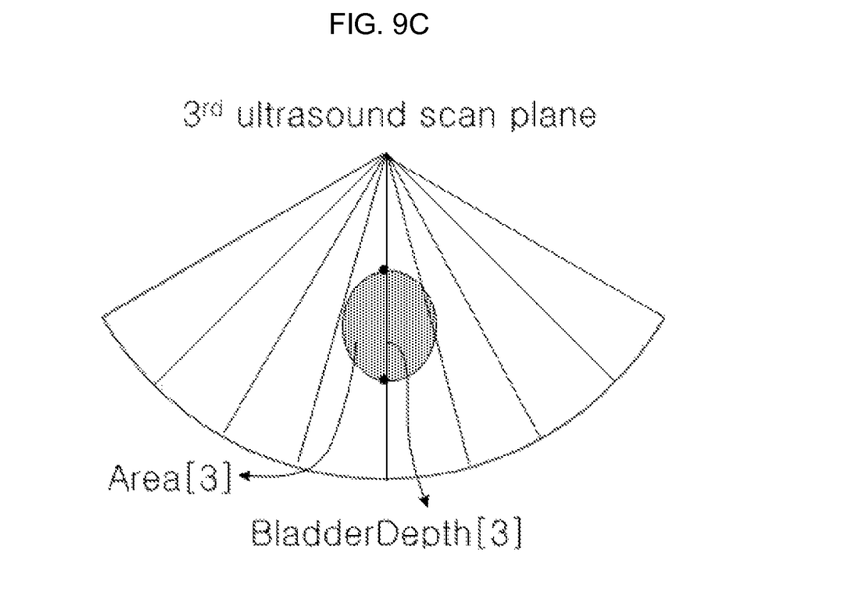
Figure 9D:
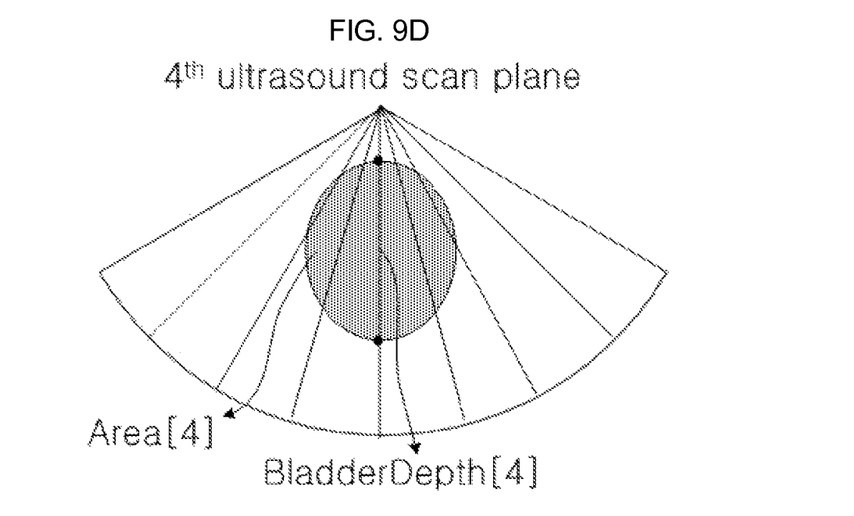

Referring to FIG. 9A, the distances between FW and BW of the bladder, 'Distance', are detected from ultrasound signals of each of scan lines constituting the i-th ultrasound scan plane at step 510.

At next step, the area of the bladder in the i-th ultrasound scan plane, Area[i], is obtained using the distance values for the scan lines constituting the i-th ultrasound scan plane at step S520. In this case, the method of obtaining an area of the bladder using the distances for scan lines may be implemented in various ways. As an example, a method of obtaining the area of a bladder may be implemented by totaling areas for sectors, each of the sectors is formed by rotating a single scan line using the rotational angle of the second stepping motor 130. As another example, a method of obtaining the area of the bladder may be implemented by totaling the areas for trapezoids, each of the trapezoids is formed by the two front walls and two back walls of the neighbored scan lines.

The virtual radius of the bladder in i-th ultrasound scan plane 'r[i]' is generated using the obtained area of the bladder 'Area[i]'. Given the assumption that the bladder is a circle, the virtual radius 'r[i]' is determined by a radius of a circle of which the area is same as the area of the bladder 'Area[i]' at step S530.

Typically, in the case of obtaining a three-dimensional volume using a plurality of two-dimensional areas, the volume smaller than an actual volume is calculated and, thus, an error occurs if scanning is performed in a state in which the center of a first rotational axis deviates from the center of the bladder. Accordingly, numerical calibration procedure is performed to reduce such error and accurately measure the volume of urine in the bladder.

A bladder depth of the bladder in i-th ultrasound scan plane 'BladderDepth[i]' is determined by the maximum value of the distances for i-th ultrasound scan plane at step S540.

The steps S510, S520, S530 and S540 are repeatedly implemented to all of the ultrasound scan planes.

Thereafter, the maximum value of the bladder depths for the ultrasound scan planes 'MaxBladderDepth' is obtained at step S560.

Thereafter, at step S570, the calibration coefficient for each of the ultrasound scan planes is obtained using the following equation 1:

$$ComFactor[i] = \frac{MaxBladderDepth}{BladderDepth[i]} \quad (1)$$

Where ComFactor[i] is the calibration coefficient for i-th ultrasound scan plane, BladderDepth[i] is the bladder depth for i-th ultrasound scan plane.

Thereafter, at step S580, calibrated radius of the bladder for each of the ultrasound scan planes is calculated using the following Equation 2:

$$ComR[i] = ComFactor[i] \times r[i] \quad (2)$$

Where, 'ComR[i]' is the calibrated radius of the bladder for i-th ultrasound scan plane.

The average value of the calibrated radii of the bladders for the ultrasound scan planes 'AverageR' is obtained at step S580. Thereafter, given the assumption that the complete bladder is a sphere, the total volume of urine 'V' in the bladder by applying the average radius 'AverageR' to the following Equation 3 is obtained at step S590.

$$V = \frac{4}{3}\pi AversageR^3 \quad (3)$$

From the above-described process, the method for measuring the volume of urine in a bladder according to the present invention can accurately detect the volume of urine in the bladder although the transducer is placed on the position which is moved from center of the bladder.

Furthermore, the apparatus of the present invention collects the ultrasonic information while automatically rotating the two stepping motors, so that it can collect all pieces of ultrasonic information within a region defined in a cone shape having a vertex at the location at which the ultrasonic scanning apparatus is disposed. As a result, the apparatus of the present invention can very accurately measure the volume of urine using ultrasonic information about a plurality of ultrasound scan planes that are spaced apart from each other and exist in an angle of 360°.

In particular, the apparatus and the method of the present invention calibrate the radii of the bladder using the calibration coefficients, which are obtained by calculating the degree to which a first detection location is moved from the center of the urinary bladder, so that it can perform accurate measurement even when the detection location is moved from the center of the urinary bladder.

Although the present invention has been described in detail in conjunction with the preferred embodiment, the present invention is described only for illustrative purposes and is not limited thereto. Those skilled in the art will appreciate that various modifications and applications, which are not described above, are possible within a range that does not change the substantial characteristics of the present invention. For example, in the present embodiment, the method of obtaining an area of a bladder for a corresponding plane using the rotational angles of the first stepping motor and the second stepping motor and ultrasonic information about the respective scan lines may be modified and implemented in various ways to improve scanning performance. Furthermore, it should be appreciated that the differences regarding the modifications and the applications are included in the scope of the present invention, which is defined by the accompanying claims.

What is claimed is:

1. An apparatus for automatically measuring a volume of urine in a bladder using ultrasound signals, comprising:
   a transducer for transmitting the ultrasound signals and receiving the ultrasound signals returning from the bladder and surrounding tissues;
   a central control unit configured to generate a plurality of ultrasound scan planes using the received ultrasound signals of the transducer, each of the ultrasound scan planes is separated by a selected angle and consists of a plurality of scan lines, to produce a scan cone for scanning the bladder;

detect distances between front and back walls of the bladder for each scan line in the ultrasound scan planes;

automatically determine an area of the bladder using the detected distances of the scan lines for each ultrasound scan plane;

automatically generate a virtual radius of the bladder using a determined area of the bladder for each ultrasound scan plane;

automatically determine a calibration coefficient for each ultrasound scan plane using the detected distances of the scan lines;

automatically calibrate the virtual radius of the bladder for each ultrasound scan plane using the calibration coefficient; and automatically determine the volume of urine in the bladder by calculating a volume of a sphere of which the radius is an average of the calibrated virtual radii for the ultrasound scan planes, wherein the central control unit is configured to determine the virtual radius of the bladder for each ultrasound scan plane by using the radius of a circle of which the area is the same as the detected area of the bladder for the corresponding ultrasound scan plane, and wherein the central control unit is configured to calculate the calibration coefficient for each ultrasound scan plane using the following equation:

$$ComFactor[i] = \frac{MaxBladderDepth}{BladderDepth[i]}$$

where ComFactor[i] is a calibration coefficient for an i-th ultrasound scan plane, BladderDepth[i] is a bladder depth for the i-th ultrasound scan plane and is determined by a maximum of distances between front wall and back wall of bladder in scan lines for the i-th ultrasound scan plane, MaxBladderDepth is determined by a maximum of the bladder depths for the ultrasound scan planes.

2. The apparatus of claim 1, wherein the virtual radius is calibrated using the following equation:

$$ComR[i] = ComFactor[i] \times r[i]$$

where, 'ComR[i]' is a calibrated virtual radius of the bladder for i-th ultrasound scan plane, 'ComFactor[i]' is a calibration coefficient for an i-th ultrasound scan plane, and 'r[i]' is a virtual radius of the bladder for i-th ultrasound scan plane.

3. A method for automatically measuring a volume of urine in a bladder using ultrasound signals, comprising the steps of:

transmitting ultrasound signals and receiving the ultrasound signals returning from the bladder and surrounding tissues;

generating a plurality of ultrasound scan planes using the received ultrasound signals, each of the ultrasound scan planes is separated by a selected angle and consists of a plurality of scan lines, to produce a scan cone for scanning the bladder;

detecting distances between front and back walls of the bladder for each scan line in the ultrasound scan planes;

determining an area of the bladder using the detected distances of the scan lines for each ultrasound scan plane;

generating a virtual radius of the bladder using a determined area of the bladder for each ultrasound scan plane;

determining a calibration coefficient for each ultrasound scan plane using the detected distances of the scan lines;

calibrating the virtual radius of the bladder for each ultrasound scan plane using the calibration coefficient;

determining the volume of urine in the bladder by calculating a volume of a sphere of which the radius is an average of the calibrated virtual radii for the ultrasound scan planes, wherein the virtual radius of the bladder for each ultrasound scan plane is determined by the radius of a circle of which the area is the same as the area of the bladder for the corresponding ultrasound scan plane, and wherein the calibration coefficient for each ultrasound scan plane is calculated using the following equation:

$$ComFactor[i] = \frac{MaxBladderDepth}{BladderDepth[i]}$$

where ComFactor[i] is a calibration coefficient for an i-th ultrasound scan plane, BladderDepth[i] is a bladder depth for the i-th ultrasound scan plane and is determined by a maximum of the distances between FW (front wall) and BW (back wall) of the bladder in the scan lines for the i-th ultrasound scan plane, MaxBladderDepth is determined by the maximum of the bladder depths in the ultrasound scan planes.

4. The method of claim 3, wherein the virtual radius is calibrated using the following equation:

$$ComR[i] = ComFactor[i] \times r[i]$$

where, 'ComR[i]' is a calibrated virtual radius of the bladder for i-th ultrasound scan plane, 'ComFactor[i]' is a calibration coefficient for an i-th ultrasound scan plane, and 'r[i]' is a virtual radius of the bladder for i-th ultrasound scan plane.

* * * * *